United States Patent
Schiene et al.

(10) Patent No.: US 10,206,890 B2
(45) Date of Patent: Feb. 19, 2019

(54) PHARMACEUTICAL COMBINATION

(71) Applicant: Gruenenthal GmbH, Aachen (DE)

(72) Inventors: Klaus Schiene, Juechen (DE); Petra Bloms-Funke, Wuerselen (DE); Thomas Christoph, Aachen (DE)

(73) Assignee: GRUENENTHAL GMBH, Aachen (DE)

(*) Notice: Subject to any disclaimer, the term of this patent is extended or adjusted under 35 U.S.C. 154(b) by 0 days.

(21) Appl. No.: 14/927,585

(22) Filed: Oct. 30, 2015

(65) Prior Publication Data

US 2016/0045458 A1 Feb. 18, 2016

Related U.S. Application Data

(63) Continuation of application No. 12/693,747, filed on Jan. 26, 2010, now abandoned, which is a continuation-in-part of application No. 12/554,235, filed on Sep. 4, 2009, now abandoned.

(60) Provisional application No. 61/094,787, filed on Sep. 5, 2008.

(30) Foreign Application Priority Data

Sep. 5, 2008 (EP) .................................... 08015625

(51) Int. Cl.
| | |
|---|---|
| *A61K 31/137* | (2006.01) |
| *A61K 31/165* | (2006.01) |
| *A61K 31/197* | (2006.01) |
| *A61K 31/205* | (2006.01) |
| *A61K 31/27* | (2006.01) |
| *A61K 31/4015* | (2006.01) |
| *A61K 31/522* | (2006.01) |
| *A61K 31/53* | (2006.01) |
| *A61K 31/70* | (2006.01) |
| *A61K 45/06* | (2006.01) |

(52) U.S. Cl.
CPC .......... *A61K 31/137* (2013.01); *A61K 31/165* (2013.01); *A61K 31/197* (2013.01); *A61K 31/205* (2013.01); *A61K 31/27* (2013.01); *A61K 31/4015* (2013.01); *A61K 31/522* (2013.01); *A61K 31/53* (2013.01); *A61K 31/70* (2013.01); *A61K 45/06* (2013.01)

(58) Field of Classification Search
CPC .. A61K 31/137; A61K 31/165; A61K 31/197; A61K 31/205; A61K 31/27; A61K 31/4015; A61K 31/522; A61K 31/53; A61K 31/70; A61K 45/06
See application file for complete search history.

(56) References Cited

U.S. PATENT DOCUMENTS

| | | |
|---|---|---|
| 487,252 A | 12/1892 | Comes |
| 2,948,718 A | 8/1960 | Schindler et al. |
| 3,652,589 A | 3/1972 | Flick et al. |
| 3,845,770 A | 11/1974 | Theeuwes et al. |
| 3,916,899 A | 11/1975 | Theeuwes et al. |
| 4,024,175 A | 5/1977 | Satzinger et al. |
| 4,034,758 A | 7/1977 | Theeuwes et al. |
| 4,077,407 A | 3/1978 | Theeuwes et al. |
| 4,132,788 A | 1/1979 | Wong |
| 4,260,629 A | 4/1981 | Schmidt et al. |
| 4,389,393 A | 6/1983 | Schor et al. |
| 4,569,937 A | 2/1986 | Baker et al. |
| 4,571,400 A | 2/1986 | Arnold |
| 4,587,252 A | 5/1986 | Arnold |
| 4,602,017 A | 7/1986 | Sawyer et al. |
| 4,612,008 A | 9/1986 | Wong et al. |
| 4,696,943 A | 9/1987 | Gobert et al. |
| 4,765,989 A | 8/1988 | Wong et al. |
| 4,783,337 A | 11/1988 | Wong et al. |
| 4,837,223 A | 6/1989 | Gobert et al. |
| 4,943,639 A | 7/1990 | Gobert et al. |
| 5,071,607 A | 12/1991 | Ayer et al. |
| 5,330,761 A | 7/1994 | Baichwal |
| 5,399,362 A | 3/1995 | Baichwal et al. |
| 5,455,046 A | 10/1995 | Baichwal |
| 5,472,711 A | 12/1995 | Baichwal |

(Continued)

FOREIGN PATENT DOCUMENTS

| | | |
|---|---|---|
| CA | 2 706 596 A1 | 5/2009 |
| CN | 102065852 A | 5/2011 |

(Continued)

OTHER PUBLICATIONS

Khoruzhaya et al., "Biophamaceutics as a Scientific Field in Development and Improvement of Medicinal Preparations", Ministry of Education and Science of the Russian Federation et al., 2006, pp. 5-13, with English translation (24 pages).

Kyiv Ministry of Public Heath of Ukraine "Quality Manual Medicines Specifications: Check Tests and Acceptance Criteria", Manual 42-3.2, 2004, p. 3, with English translation (5 pages).

Rauschkolb-Loeffler et al., "Efficacy and Tolerability of Tapentadol for Relief of Moderate-to-Severe Chronic Pain Due to Osteoarthritis of the Knee", Ann Rheum Dis, 2007, vol. 66, suppl. II, p. 507 (one (1) sheet).

(Continued)

*Primary Examiner* — Sarah Pihonak

(74) *Attorney, Agent, or Firm* — Norris McLaughlin P.A.

(57) ABSTRACT

A composition of matter comprising in combination as component (a) at least one 3-(3-dimethylamino-1-ethyl-2-methyl-propyl)phenol compound, and as component (b) at least one antiepileptic, a pharmaceutical formulation and a dosage form comprising said composition of matter, and a method of treating pain, e.g. neuropathic pain, in which components (a) and (b) are administered simultaneously or sequentially to a mammal, whereby component (a) may be administered before or after component (b) and whereby components (a) or (b) are administered to the mammal either via the same or a different pathway of administration.

25 Claims, No Drawings

(56) References Cited

U.S. PATENT DOCUMENTS

| | | | |
|---|---|---|---|
| 6,127,418 | A | 10/2000 | Bueno et al. |
| 6,248,737 | B1 | 6/2001 | Buschmann et al. |
| 6,326,374 | B1 | 12/2001 | Magnus et al. |
| 6,451,857 | B1 | 9/2002 | Hurtt et al. |
| 6,593,368 | B2 | 7/2003 | Magnus-Miller et al. |
| 6,680,071 | B1 | 1/2004 | Johnson et al. |
| RE39,593 | E | 4/2007 | Buschmann et al. |
| 2002/0010178 | A1 | 1/2002 | Buschmann et al. |
| 2002/0115705 | A1 | 8/2002 | Magnus-Miller et al. |
| 2003/0035053 | A1 | 2/2003 | Kyuma et al. |
| 2003/0059466 | A1 | 3/2003 | Seth |
| 2005/0038062 | A1 | 2/2005 | Burns et al. |
| 2005/0058706 | A1 | 3/2005 | Bartholomaeus et al. |
| 2006/0099249 | A1 | 5/2006 | Seth et al. |
| 2007/0254960 | A1 | 11/2007 | Bloms-Funke et al. |
| 2009/0099138 | A1 | 4/2009 | Schiene et al. |
| 2012/0034304 | A1 | 2/2012 | Bartholomaeus et al. |
| 2014/0242169 | A1 | 8/2014 | Sesha |
| 2017/0216212 | A1 | 8/2017 | Sesha |

FOREIGN PATENT DOCUMENTS

| | | | |
|---|---|---|---|
| DE | 24 60 891 A1 | 12/1974 | |
| DE | 24 60 891 A1 | 7/1976 | |
| EP | 0 021 121 A1 | 1/1981 | |
| EP | 0 162 036 A1 | 11/1985 | |
| EP | 0 534 628 A1 | 3/1993 | |
| EP | 0 693 475 A1 | 1/1996 | |
| EP | 1 944 022 A1 | 7/2008 | |
| JP | 2011-504509 A | 2/2011 | |
| JP | 5731387 B2 | 6/2015 | |
| KR | 10-2002-0025221 A | 4/2002 | |
| KR | 101607112 | 12/2010 | |
| WO | WO 8400490 A1 * | 2/1984 | ........... A61K 31/485 |
| WO | WO 99/12537 A1 | 3/1999 | |
| WO | WO 01/13904 A2 | 3/2001 | |
| WO | 03/035053 | 5/2003 | |
| WO | WO 03/035053 A1 | 5/2003 | |
| WO | WO 03/061656 A1 | 7/2003 | |
| WO | 2004047823 | 6/2004 | |
| WO | WO 2007/005716 A2 | 1/2007 | |
| WO | 2007079195 | 7/2007 | |
| WO | WO 2007/087452 A2 | 8/2007 | |
| WO | WO 2007/087452 A3 | 8/2007 | |
| WO | WO 2007/128412 A1 | 11/2007 | |
| WO | WO 2008/027442 A2 | 3/2008 | |
| WO | WO 2009/067703 A2 | 5/2009 | |
| WO | WO 2009/067703 A3 | 5/2009 | |
| WO | WO 2009/082039 A1 | 7/2009 | |
| WO | WO 2010/025931 A2 | 3/2010 | |

OTHER PUBLICATIONS

Freynhagen et al., "Efficacy of pregabalin in neuropathic pain evaluated in a 12-week, randomised, double-blind, multicentre, placebo-controlled trial of flexible-and fixed-dose regimens", Pain, 2005, vol. 115, pp. 254-263 (ten (10) sheets).
A. E. Takemori, "Pharmacologic Factors which Alter the Action of Narcotic Analgesics and Antagonists", Annals New York Academy of Sciences, 1976, pp. 262-272 (eleven (11) sheets).
Woodbury et al., "Drugs Effective in the Therapy of the Epilepsies", 1975, chapter 13, pp. 201-226 (fifteen (15) sheets).
Webb et al., "The addition of a tramadol infusion to morphine patient-controlled analgesia after abdominal surgery: a double-blinded, placebo-controlled randomized trial", Anesth Analg, 2002, vol. 95, pp. 1713-1718 (six (6) sheets).
Terlinden et al., "Absorption, metabolism, and excretion of 14C-labeled tapentadol HCl in healthy male subjects", European Journal of Drug Metabolism and Pharmacokinetics, 2007, vol. 32, No. 3, pp. 163-169 (seven (7) sheets).
Taber et al., "Agonist and antagonist interactions of opioids on acetic acid-induced abdominal stretching in mice", The Journal of Pharmacology and Experimental Therapeutics, 1969, vol. 169, No. 1, pp. 29-38 (ten (10) sheets).
Stacher et al., "Effects of tolmetin, paracetamol, and of two combinations of tolmetin and paracetamol as compared to placebo on experimentally induced pain. A double blind study", International Journal of Clinical Pharmacology and Biopharmacy, 1979, vol. 17, No. 6, pp. 250-255 (six (6) sheets).
Pircio et al., "Pharmacological effects of a combination of butorphanol and acetaminophen", Arch. Int. Pharmacodyn, 1978, vol. 235, pp. 116-123 (eight (8) sheets).
M. Langman, "Ulcer Complications and Nonsteroidal Anti-Inflammatory Drugs", The American Journal of Medicine, 1988, vol. 84, suppl. 2A, pp. 15-19 (five (5) sheets).
P. Insel, "Analgesic-Antipyretics and Antiinflammatory Agents; Drugs Employed in the Treatment of Rheumatoid Arthritis and Gout", 1990, Chapter 26, pp. 638-681 (forty-four (44) sheets).
C. Larsen et al., Design and application of prodrugs, Textbook of Drug Design and Discovery, Chpt. 14, pp. 411-458, 2002 (48 sheets).
Aronson et al., "Nonsteroidal Anti-Inflammatory Drugs, Traditional Opioids, and Tramadol: Contrasting Therapies for the Treatment of Chronic Pain," Clinical Therapeutics, 1997, pp. 420-432, vol. 19, No. 3 (13 sheets).
Belikov, "Pharmaceutical Chemistry: Connection Between Molecular Structures of Substances and Action Thereof on the Body," General Pharmaceutical Chemistry, 1993, $2^{nd}$ edition (five (5) sheets).
Kharkevich, "Pharmacology: Dependence of Pharmacotherapeutic Effect from Properties of Drugs and Conditions of Use Thereof; a) Chemical Structure, Physico-Chemical and Physical Properties of Drugs," 1987, $3^{rd}$ edition (three (3) sheets).
Kharkevich, "Pharmacology: d) Interaction of Drugs; Pharmacological Interaction," 1987, $3^{rd}$ edition, (eight (8) sheets).
Sergeyev, "Short Course of Molecular Pharmacology," Ministry of Public Health of the RSFSR II Moscow Medicinal Institute Named After N.I. Pirogov, 1975 (three (3) sheets).
Mark D. Aronson, "Nonsteroidal Anti-Inflammatory Drugs, Traditional Opioids, and Tramadol: Contrasting Therapies for the Treatment of Chronic Pain", Clinical Therapeutics, vol. 19, No. 3, 1997, pp. 420-432.
Lyrica capsules package insert, retrieved from the internet on Nov. 27, 2015, pp. 2-9.
I. Gilron et al., "D15—Opioids in Non-Cancer Pain: (733) Randomized controlled trial of a morphine-gabapentin combination in neuropathic pain", Abstracts, 2005 (one (1) page).
Elina M. Tiippana et al., "Do Surgical Patients Benefit from Perioperative Gabapentin/Pregabalin ? A Systematic Review of Efficacy and Safety", Anesthesia & Analgesia, vol. 104, No. 6, Jun. 2007, pp. 1545-1556.
Ian Gilron et al., "Morphine, Gabapentin, or Their Combination for Neuropathic Pain", The New England Journal of Medicine, vol. 352, No. 13, Mar. 31, 2005, pp. 1324-1334.
Gilron et al., "Combination pharmacotherapy for neuropathic pain: current evidence and future directions", Expert Rev. Neurotherapeutics 5(6), 2005, pp. 823-830.
Nishiyama et al., "Effects of Intrathecal NMDA and Non-NMDA Attagonists on Acute Thermal Nociception and Their Interaction with Morphine", American Society of Anesthesiologists, Inc., 1998, pp. 715-722 (8 pages).
O. Mimoz et al., Analgesic efficacy and safety of nefopam vs. propacetamol following hepatic resection, Department of Anaesthesia and Pain Management, Paul Brousee Hopsital, Villejuif, France, 2001, 56, pp. 520-525 (6 pages).
Russian language Office Action issued in counterpart Russian Patent Application No. 2014138166 dated Jul. 14, 2017 with English translation (eleven (11) pages).
Tallarida et al., "Statistical Analysis of Drug-Drug and Site-Site Interactions with Isobolograms", Life Sciences, vol. 45, pp. 947-961 (15 pages).
Kim et al., "An experimental model for peripheral neuropathy produced by segmental spinal nerve ligation in the rat", Marine Biomedical Institute and Department of Anatomy and Neurosciences and of Physiology and Biophysics, 1992, pp. 355-363 (9 pages).

(56) References Cited

OTHER PUBLICATIONS

Gennaro, "Pharmaceutical Sciences", 1985, Remington's, four (4) pages total.
Tzschentke et al., "(−)-(1R,2R)-3-(3-Dimethylamino-1-ethyl-2-methyl-propyl)-phenol Hydrochloride (Tapentadol HCl): a Novel μ-Opioid Receptor Agonist/Norepinephrine Reuptake Inhibitor with Broad Spectrum Analgesic Properties", The Journal of Pharmacology and Experimental Therapeutics, 2007, pp. 265-276, vol. 323, No. 1.
The Textbook of Pharmaceutical Medicine, 6$^{th}$ Edition, 2006, Wiley-Blackwell, p. 160.
Correa, "Guidelines for the examination of pharmaceutical patents: Developing a public health perspective"; 2007; ICTSD.
Correa, "Pautas para el examen de patents farmaceuticas"; Mar. 2008, ICTSD.
Vengerovsky, "Pharmacological Incompatibility"; Lecture for Physicians, Bulletin of Siberian Medicine, 3, 2003 and English translation.
Alyatdin, Pharmacology: University Textbook; Chapter 3, 70-71, 2004 (English translation provided).
Avoxa-Mediengruppe Deutscher Apotheker GmbH, 2013, 1-3 Neuropathic pain: solo or double-act therapy?; (English translation provided).
Cheng, et al., "Antiallodynic Effect of Intrathecal Gabapentin and its Interaction with Clonidine in a Rat Model of Postoperative Pain"; Anesthesiology, 2000, 92, pp. 1126-1131.
Cui Zhan, China Academic Journal, 2006, 2910-2911—English translation also provided.
Tzschentke et al., "Tapentadol Hydrochloride"; Drugs of the Future 2006, 31 (12), 1053-1061.

\* cited by examiner

PHARMACEUTICAL COMBINATION

CROSS REFERENCE TO RELATED APPLICATIONS

This application is a continuation of application Ser. No. 12/693,747, filed Jan. 26, 2010, which is a continuation-in-part of co-pending application Ser. No. 12/554,235, filed Sep. 4, 2009 which claims priority from U.S. provisional patent application No. 61/094,787, filed Sep. 5, 2008. Priority is also claimed based on European patent application no. EP 08 015 625.0, filed Sep. 5, 2008.

BACKGROUND OF THE INVENTION

The present invention relates to a combination comprising as components (a) at least one 3-(3-dimethylamino-1-ethyl-2-methyl-propyl)phenol compound, and (b) at least one antiepileptic, a pharmaceutical formulation and a dosage form comprising said combination as well as a method of treating pain, e.g. neuropathic pain, wherein components (a) and (b) are administered simultaneously or sequentially to a mammal, whereby component (a) may be administered before or after component (b) and whereby components (a) or (b) are administered to the mammal either via the same or a different pathway of administration.

The treatment of chronic and acute pain conditions is extremely important in medicine. There is currently a worldwide demand for additional, not exclusively opioid-based, but highly effective pain treatment. The urgent need for action for patient-oriented and purposeful treatment of pain conditions, this being taken to mean the successful and satisfactory treatment of pain for the patient, is documented in the large number of scientific papers which have recently appeared in the field of applied analgesics and fundamental research work on nociception.

Even if the analgesics that are currently used for treating pain, for example opioids, NA- and 5HT-reuptake inhibitors, NSAIDS and COX inhibitors, are analgesically effective, side effects nevertheless sometimes occur. WO 01/13904 describes substance combinations comprising a tramadol material and an anticonvulsant drug, which show super-additive effects upon administration. Due to the super-additive effect the overall dose and accordingly the risk of undesired side effects can be reduced.

SUMMARY OF THE INVENTION

Thus, it was an object of the present invention to find further combinations having improved properties. It was also an object of the present invention to find further combinations that are suitable for the treatment of pain and which preferably exhibit fewer undesired side effects compared to its individual components, if administered in effective doses.

It has been found that a combination comprising (a) at least one 3-(3-dimethylamino-1-ethyl-2-methyl-propyl)-phenol compound, and (b) at least one antiepileptic exhibits an analgesic effect. If these components are present in the composition in such a weight ratio that a supra-additive or synergistic effect is observed upon administration to the patients, the overall administered dose may be lowered, so that fewer undesired side-effects will occur.

Accordingly, the present invention relates to a pharmaceutical combination comprising as components
(a) 3-(3-Dimethylamino-1-ethyl-2-methyl-propyl)phenol of formula (I)

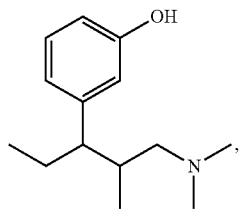

optionally in form of one of its pure stereoisomers, in particular an enantiomer or a diastereomer, a racemate or in form of a mixture of its stereoisomers, in particular enantiomers and/or diastereomers in any mixing ratio, or any corresponding acid addition salt thereof, and
(b) at least one antiepileptic.

In another embodiment the present invention relates to a pharmaceutical combination comprising as components
(a) 3-(3-Dimethylamino-1-ethyl-2-methyl-propyl)phenol of formula (I)

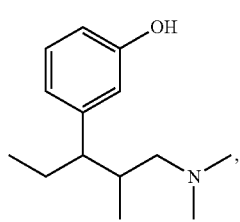

optionally in form of one of its pure stereoisomers, in particular an enantiomer or a diastereomer, a racemate or in form of a mixture of its stereoisomers, in particular enantiomers and/or diastereomers in any mixing ratio, or any corresponding acid addition salt thereof, and
(b) at least one antiepileptic and/or at least one compound selected from the group consisting of voltage dependent calcium channel blockers, voltage dependent t-type calcium channel blockers, voltage dependent sodium channel blockers, compounds that exhibit enhancement of fast or slow inactivation of voltage dependent sodium channels, KCNQ channel openers, SV2A ligands, modulators of collapsin response mediator protein-2 (CRMP-2), glutamate release inhibitors, AMPA receptor antagonists, NMDA antagonists, GABA receptor modulators, GABA aminotransferase inhibitors, GABA reuptake inhibitors and carbonic anhydrase inhibitors.

In one embodiment of the inventive combination the compound of formula (I) is selected from the group consisting of:
  (1R,2R)-3-(3-dimethylamino-1-ethyl-2-methyl-propyl)-phenol,
  (1S,2S)-3-(3-dimethylamino-1-ethyl-2-methyl-propyl)-phenol,
  (1R,2S)-3-(3-dimethylamino-1-ethyl-2-methyl-propyl)-phenol,
  (1S,2R)-3-(3-dimethylamino-1-ethyl-2-methyl-propyl) phenol, and any mixture thereof.

In another embodiment of the inventive combination the compound of formula (I) is selected from (1R,2R)-3-(3-dimethylamino-1-ethyl-2-methyl-propyl) phenol, and
(1S,2S)-3-(3-dimethylamino-1-ethyl-2-methyl-propyl) phenol, and any mixture thereof.

In yet another embodiment the inventive combination comprises
(a) the compound (1R,2R)-3-(3-dimethylamino-1-ethyl-2-methyl-propyl)-phenol of formula (I),

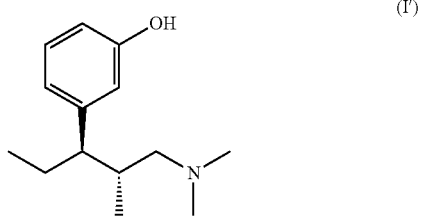 [SMILES: CC[C@@H](c1cccc(O)c1)[C@@H](C)CN(C)C]

(I')

or an acid addition salt thereof, and
(b) at least one antiepileptic.

The compound 3-(3-dimethylamino-1-ethyl-2-methyl-propyl)-phenol of formula (I), its stereoisomers and corresponding salts thereof as well as methods for their preparation are well known, for example, from U.S. Pat. No. 6,248,737 B1, the entire disclosure of which is incorporated herein by reference.

The definition of component (a) as used herein includes 3-(3-dimethylamino-1-ethyl-2-methyl-propyl)-phenol, derivatives thereof and stereoisomers thereof in any possible form, thereby particularly including solvates and polymorphs, salts, in particular acid addition salts and corresponding solvates and polymorphs.

The term derivative as used herein particularly includes prodrugs such as ethers and esters of the active substance. Suitable methods for selecting and preparing a pro-drug of a given substance are for example described in "Textbook of Drug Design and Discovery", 3$^{rd}$ edition, 2002, chapter 14, pages 410-458, Editors: Krogsgaard-Larsen et al., Taylor and Francis. The respective parts of said literature description are incorporated by reference and form part of the present disclosure.

If component (a) is present as mixture of enantiomers, such a mixture may contain the enantiomers in racemic or non-racemic form. A non-racemic form could, for example, contain the enantiomers in a ratio of 60±5:40±5, 70±5:30±5, 80±5:20±5 or 90±5:10±5.

The term "isolated" as used herein with regard to stereoisomers (e.g., enantiomers or diastereomers) means that the respective stereoisomer is separated from other stereoisomers but not necessarily from other substances.

The compound 3-(3-dimethylamino-1-ethyl-2-methyl-propyl)phenol and its stereoisomers according to component (a) may be present in the inventive pharmaceutical composition in form of an acid addition salt, whereby any suitable acid capable of forming such an addition salt may be used.

The conversion of 3-(3-dimethylamino-1-ethyl-2-methyl-propyl)phenol into a corresponding addition salt, for example, via reaction with a suitable acid may be effected in a manner known to persons skilled in the art. Suitable acids include, but are not limited to, hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. Salt formation is preferably effected in a solvent, for example, diethyl ether, diisopropyl ether, alkyl acetates, acetone and/or 2-butanone. Moreover, trimethylchlorosilane in aqueous solution is also suitable for the preparation of hydrochlorides.

Voltage dependent calcium channel blockers such as blockers of the alpha 2 delta subunits, voltage dependent t-type calcium channel blockers, voltage dependent sodium channel blockers, compounds that exhibit enhancement of fast or slow inactivation of voltage dependent sodium channels, KCNQ channel openers, SV2A ligands, modulators of collapsin response mediator protein-2 (CRMP-2), glutamate release inhibitors, AMPA receptor antagonists, NMDA antagonists, GABA receptor modulators such as GABA A receptor inhibitors, GABA B receptor inhibitors, benzodiazepams and barbiturates, GABA aminotransferase inhibitors (GABA-transaminase inhibitors), GABA reuptake inhibitors and carbonic anhydrase inhibitors are well known to those skilled in the art. For these aforementioned compounds general ranges of potency with regard to the respective mechanisms are well known to persons skilled in the art, as are suitable assays for their determination.

In one embodiment the potency of the voltage dependent calcium channel blockers such as blockers of the alpha 2 delta subunits, expressed in $K_i$ for the displacement of [3H-Gabapentin] in the respective binding test, may be in the range of 0.001 to 0.01 µM.

In another embodiment the potency of the voltage dependent sodium channel blocker, expressed in $IC_{50}$ may be in the range of 0.1 to 500 µM.

In yet another embodiment the potency of the carbonic anhydrase inhibitor may be in the range of 0.1 to 100 nM, $IC_{50}$ for the inhibition.

In still another embodiment the potency of the glutamate release inhibitor may be in the range of 1 to 50 µM, $IC_{50}$ for the inhibition.

In a further embodiment the potency of the SV2A ligand, expressed in $pK_i$ for the binding affinity to SV2A protein, can be in the range of 0.05 to 5 µM.

In another embodiment the potency of the KCNQ channel opener, expressed as $EC_{50}$, can be in the range of 0.1 to 10 µM.

In a further embodiment the modulator of collapsin response mediator protein-2 (CRMP-2) may have a potency in the range of 1 to 50 µM, expressed as $K_i$ for its respective binding affinity.

In another embodiment the potency of the compound that exhibits enhancing slow inactivation of voltage gated sodium channels may be characterized by an $IC_{50}$ in the range of 10 to 500 µM.

Antiepileptics, which are often also referred to as anticonvulsants, are well known in the art and include, without limitation, barbiturates and derivatives, such as methylphenobarbital, phenobarbital, primidone, barbexaclone and metharbital; hydantoin derivatives such as ethotoin, phenytoin, amino(diphenylhydantoin)valeric acid, mephenytoin and fosphenytoin; oxazolidine derivatives such as paramethadione, trimethadione and ethadione; succinimide derivatives such as ethosuximide, phensuximide and mesuximide; benzodiazepine derivatives such as clonazepam; carboxamide derivatives such as carbamazepine, oxcarbazepine, eslicarbazepine and rufinamide; fatty acid derivatives such as valproic acid, valpromide, aminobutyric acid, vigabatrin, progabide and tiagabine; or other antiepileptics such as sultiame, phenacemide, lamotrigine, felbamate, topiramate, gabapentin, pheneturide, levetiracetam, brivaracetam, selectracetam, zonisamide, pregabalin, stiripentol, lacosamide and beclamide.

These aforementioned classes of antiepileptics and most of their individual representatives are, for example, listed in the Anatomical Therapeutic Chemical (ATC) classification under [N03] as used by the WHO for classification of pharmaceutically active ingredients (preferred edition: January 2008 or 2009). With regard to further details of the ATC-index reference is made to U. Fricke, J. Günther, Anatomisch-therapeutisch-chemische Klassifikation mit Tagesdosen für den deutschen Arzneimittelmarkt: Methodik der ATC-Klassifikation and DDD-Festlegung. ATC-Index mit DDD-Angaben, Wissenschaftliches Institut der AOK; and Swiss Pharmaceutical Society, Index Nominum: International Drug Directory, CRC Press; 18th edition (Jan. 31, 2004). Other suitable antiepileptics include, for example, mexiletin, retigabin and ralfinamide.

Some antiepileptics are known to be useful in the treatment of neuropathic pain. In one embodiment of the present invention one or more of these antiepileptics is used as component (b).

Also included are stereoisomers, salts, solvates, polymorphs and derivatives of the antiepileptic component as well as mixtures of any of the foregoing.

In one embodiment of the inventive combination the antiepileptic according to component (b) is selected from the group consisting of pregabalin, gabapentin, topiramate, lamotrigine, carbamazepine, oxcarbamazepine, eslicarbazepine, mexiletin, lacosamide, phenytoin, levetiracetam, brivaracetam, selectracetam, retigabin, valproic acid and ralfinamide.

In another embodiment of the inventive combination the antiepileptic according to component (b) is selected from the group consisting of pregabalin, gabapentin, topiramate, lamotrigine, carbamazepine, mexiletin, lacosamide, phenytoin, levetiracetam, retigabin, valproic acid and ralfinamide.

In still another embodiment of the inventive combination the antiepileptic according to component (b) is selected from the group consisting of pregabalin, gabapentin, topiramate, lamotrigine, lacosamide, levetiracetam and retigabine.

In another embodiment of the inventive combination the antiepileptic according to component (b) is pregabalin.

In yet another embodiment of the inventive combination the antiepileptic according to component (b) is (S)-pregabalin.

In a further embodiment of the inventive combination the antiepileptic according to component (b) is gabapentin.

In yet another embodiment of the inventive combination the antiepileptic according to component (b) is topiramate.

In still another embodiment of the inventive combination the antiepileptic according to component (b) is lamotrigine.

In yet still another embodiment of the inventive combination the antiepileptic according to component (b) is lacosamide.

In another embodiment of the inventive combination the antiepileptic according to component (b) is levetiracetam.

In yet another embodiment of the inventive combination the antiepileptic according to component (b) is retigabine.

In still another embodiment of the inventive combination the antiepileptic according to component (b) is retigabine dihydrochloride.

A specific embodiment of the present invention is a combination comprising (a) (1R,2R)-3-(3-dimethylamino-1-ethyl-2-methyl-propyl)-phenol, or an acid addition salt thereof such as the hydrochloride addition salt, and (b) one or more antiepileptics selected from the group consisting of pregabalin, gabapentin, topiramate, lamotrigine, carbamazepine, oxcarbamazepine, eslicarbazepine, mexiletin, lacosamide, phenytoin, levetiracetam, brivaracetam, selectracetam, retigabin, valproic acid and ralfinamide.

A specific embodiment of the present invention is a combination comprising (a) (1R,2R)-3-(3-dimethylamino-1-ethyl-2-methyl-propyl)-phenol, or an acid addition salt thereof such as the hydrochloride addition salt, and (b) one or more antiepileptics selected from the group consisting of pregabalin, gabapentin, topiramate, lamotrigine, carbamazepine, mexiletin, lacosamide, phenytoin, levetiracetam, retigabin, valproic acid and ralfinamide.

Another specific embodiment of the present invention is a combination comprising (a) (1R,2R)-3-(3-Dimethylamino-1-ethyl-2-methyl-propyl)-phenol, or an acid addition salt thereof such as the hydrochloride addition salt, and (b) one or more antiepileptics selected from the group consisting of pregabalin, gabapentin, topiramate, lamotrigine, lacosamide, levetiracetam and retigabine.

Another specific embodiment of the present invention is a combination comprising (a) (1R,2R)-3-(3-dimethylamino-1-ethyl-2-methyl-propyl)-phenol, or an acid addition salt thereof such as the hydrochloride addition salt, and (b) pregabalin.

Yet another specific embodiment of the present invention is a combination comprising (a) (1R,2R)-3-(3-dimethylamino-1-ethyl-2-methyl-propyl)-phenol, or an acid addition salt thereof such as the hydrochloride addition salt, and (b) (S)-pregabalin.

Some antiepileptics comprise functional groups, for example, acidic groups such as carboxy groups which are capable of forming salts with the 3-(3-dimethylamino-1-ethyl-2-methyl-propyl)-phenol component of formula (I), thereby incorporating both components (a) and (b) in one and the same salt. Thus, in another embodiment of the present invention the inventive combination comprises components (a) and (b) in form of a salt formed from these two components. Such a salt formation may be partial, i.e. the inventive composition comprises one or both of these components also in their non-salt form, or the salt formation may essentially be complete.

Both components (a) and (b) as part of the inventive combination may be administered in amounts up to their maximum daily dosage, which is known to those skilled in the art. The compound Pregabalin may preferably be administered to a patient in a daily dosage of 1 to 1200 mg, the compound Gabapentin may preferably be administered to a patient in a daily dosage of 1 to 5000 mg. The compound Topiramate may preferably be administered to a patient in a daily dosage of 1-800 mg; the compound Levetiracetam may preferably be administered to a patient in a daily dosage of 1-4500 mg; the compound Lacosamide may preferably be administered to a patient in a daily dosage of 1-800 mg; the compound Lamotrigine may preferably be administered to a patient in a daily dosage of 1-1200 mg, and the compound Retigabine may preferably be administered to a patient in a daily dosage of 1-2400 mg.

The compound (1R,2R)-3-(3-dimethylamino-1-ethyl-2-methyl-propyl)phenol may preferably be administered to a patient in a daily dosage of 25 to 1000 mg, particularly preferably in a dosage of 50 to 800 mg, more particularly preferably in a dosage of 100 to 600 mg.

In another embodiment the compound (1R,2R)-3-(3-Dimethylamino-1-ethyl-2-methyl-propyl)-phenol may preferably be administered to a patient in a daily dosage of 5 to 1000 mg, particularly preferably in a dosage of 25 to 800 mg, more particularly preferably in a dosage of 50 to 600 mg.

In one embodiment of the present invention the inventive combination may comprise 1 to 500 mg Tapentadol and 1 to 660 mg Pregabalin. This combination may, for example, be administered to the patient once daily, twice daily or three times daily.

In another embodiment of the present invention the inventive combination may comprise 1 to 500 mg Tapentadol and 1 to 1000 mg Gabapentin. This combination may, for example, be administered to the patient once daily, twice daily or three times daily.

In another embodiment of the present invention the inventive combination may comprise 1 to 500 mg Tapentadol and 1 to 400 mg Topiramate. This combination may, for example, be administered to the patient once daily, twice daily or three times daily.

In another embodiment of the present invention the inventive combination may comprise 1 to 500 mg Tapentadol and 1 to 600 mg Lamotrigine. This combination may, for example, be administered to the patient once daily, twice daily or three times daily.

In another embodiment of the present invention the inventive combination may comprise 1 to 500 mg Tapentadol and 1 to 400 mg Lacosamide. This combination may, for example, be administered to the patient once daily, twice daily or three times daily.

In another embodiment of the present invention the inventive combination may comprise 1 to 500 mg Tapentadol and 1 to 1000 mg Levetiracetam. This combination may, for example, be administered to the patient once daily, twice daily or three times daily.

In another embodiment of the present invention the inventive combination may comprise 1 to 500 mg Tapentadol and 1 to 1000 mg Retigabine. This combination may, for example, be administered to the patient once daily, twice daily or three times daily.

When administered as part of the inventive combination the administered amount per day of component (a) and/or component (b) may be less than the respective maximum daily dosage and be, for example, 75±15 wt.-%, 75±10 wt.-%, 75±5 wt.-%, 50±15 wt.-%, 50±10 wt.-%, 50±5 wt.-%, 25±15 wt.-%, 25±10 wt.-% and 25±5 wt.-% for each of the components.

In another embodiment of the present invention the inventive combination may contain components (a) and (b) essentially in an equieffective ratio.

In yet a further embodiment of the inventive combination components (a) and (b) are present in such a weight ratio that the resulting composition will exert a supra-additive or synergistic effect upon administration to a patient. Suitable weight ratios can be determined by methods well known to those skilled in the art.

Both components (a) and (b) may also be present in the inventive combination in ratios deviating from the equieffective ratio. For, example, each of the components could be present in a range from 1/50 of the equieffective amount to 50 times the equieffective amount, from 1/20 of the equieffective amount to 20 times the equieffective amount, from 1/10 of the equieffective amount to 10 times the equieffective amount, from 1/5 of the equieffective amount to 5 times the equieffective amount, from 1/4 of the equieffective amount to 4 times the equieffective amount, from 1/3 of the equieffective amount to 3 times the equieffective amount, or from 1/2 of the equieffective amount to 2 times the equieffective amount.

In another embodiment of the present invention the components (a) and (b) can be administered in a specific dosage regimen to treat pain, for example, neuropathic pain. Components (a) and (b) may be administered simultaneously or sequentially to one another, in each case via the same or different administration pathways.

Another aspect of the present invention is therefore a method of treating pain, characterized in that components (a) and (b) are administered simultaneously or sequentially to a mammal, wherein component (a) may be administered before or after component (b) and wherein components (a) or (b) are administered to the mammal either via the same or a different pathway of administration.

The term pain as used herein includes but is not limited to inflammatory pain, neuropathic pain, acute pain, chronic pain, visceral pain, migraine pain and cancer pain.

Suitable pathways of administration include but are not limited to oral, intravenous, intraarterial, intraperitoneal, intradermal, transdermal, intrathekal, intramuscular, intranasal, transmucosal, subcutaneous, and rectal administration.

The inventive combinations are toxicologically safe and are therefore suitable for the treatment of mammals, particularly humans including infants, children and grown-ups. Thus, in a further aspect the present invention relates to a pharmaceutical composition comprising an inventive combination as described herein and one or more auxiliary agents.

In a further aspect the present invention relates to a pharmaceutical dosage form comprising an inventive combination as described herein and one or more auxiliary agents. In one embodiment the inventive pharmaceutical dosage form additionally comprises caffeine.

In one embodiment, the pharmaceutical dosage form of the invention is suitable for being administered orally, intravenously, intraarterially, intraperitoneally, intradermally, transdermally, intrathekally, intramuscularly, intranasally, transmucosally, subcutaneously, or rectally.

The formulations and dosage forms of the invention may contain auxiliary agents, for example, carriers, fillers, solvents, diluents, colorants and/or binders. The selection of auxiliary agents and of the amounts of the same to be used depends, for example, on how the drug is to be administered, e.g. orally, intravenously, intraarterially, intraperitoneally, intradermally, transdermally, intramuscularly, intranasally or locally, for example for infections of the skin, of the mucous membranes or of the eye.

Suitable auxiliary agents in the context of this invention include any substances known to persons skilled in the art to be useful for the preparation of galenical formulations. Examples of suitable auxiliary agents include, but are not limited to, water, ethanol, 2-propanol, glycerol, ethylene glycol, propylene glycol, polyethylene glycol, polypropylene glycol, glucose, fructose, lactose, saccharose, dextrose, molasses, starch, modified starch, gelatine, sorbitol, inositol, mannitol, microcrystalline cellulose, methyl cellulose, carboxymethyl cellulose, cellulose acetate, shellac, cetyl alcohol, polyvinyl pyrrolidone, paraffins, waxes, natural and synthetic gums, acacia gum, alginates, dextran, saturated and unsaturated fatty acids, stearic acid, magnesium stearate, zinc stearate, glycerol stearate, sodium lauryl sulfate, edible oils, sesame oil, coconut oil, peanut oil, soybean oil, lecithin, sodium lactate, polyoxyethylene and polypropylene fatty acid ester, sorbitan fatty acid ester, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talcum, kaolin, pectin, crosspovidone, agar and bentonite.

Pharmaceutical formulations (dosage forms) in the form of tablets, effervescent tablets, chewing tablets, dragees, capsules, drops, juices or syrups are, for example, suitable for oral administration. Oral pharmaceutical formulations may also be in the form of multiparticulates such as granules, pellets, spheres, crystals and the like, optionally compressed into a tablet, filled into a capsule, filled into a sachet or suspended in a suitable liquid medium. Oral pharmaceutical formulations may also be equipped with an enteric coating.

Pharmaceutical formulations that are suitable for parenteral, topical and inhalative administration include but are not limited to solutions, suspensions, easily reconstitutable dry preparations and sprays. Suppositories are a suitable pharmaceutical formulation for rectal administration. Formulations in a deposit, in dissolved form, for example, in a patch optionally with the addition of agents to promote skin penetration, are examples of suitable formulations for percutaneous administration.

One or both of the components (a) and (b) may be present in the inventive pharmaceutical formulation at least partially in controlled-release form. Moreover, any controlled release/immediate release combination of said components may also be present in the inventive pharmaceutical formulation. For example, one or both of the components may be released from the inventive formulations with a certain delay, e.g. if administered orally, rectally or percutaneously. Such formulations are particularly useful for "once-daily" or "twice-daily" preparations, which only have to be taken once a day, respectively, twice a day. Suitable controlled-release materials are well known to those skilled in the art.

The pharmaceutical formulations of the invention may be produced using materials, means, devices and processes that are well known in the prior art of pharmaceutical formulations, as described for example in "Remington's Pharmaceutical Sciences", A. R. Gennaro (ed.), $17^{th}$ edition, Mack Publishing Company, Easton, Pa. (1985), in particular in part 8, chapters 76 to 93.

In order to obtain a solid pharmaceutical formulation such as a tablet, for example, the components of the pharmaceutical composition may be granulated with a pharmaceutical carrier, for example conventional tablet ingredients such as corn starch, lactose, saccharose, sorbitol, talcum, magnesium stearate, dicalcium phosphate or pharmaceutically acceptable gums, and pharmaceutical diluents, for example water, in order to form a solid composition that contains the components in homogeneous distribution. The term "homogeneous distribution" is taken to mean that the components are distributed uniformly over the entire composition, so that said composition may easily be divided into equally effective unit dose forms, such as tablets, pills or capsules and the like. The solid composition is then divided into unit dose forms. The tablets or pills of the pharmaceutical composition according to the invention may also be coated or compounded in a different manner, in order to provide a dose form with a controlled release.

If one of the components is to be released prior to the other component, for example at least 30 minutes or 1 hour beforehand, pharmaceutical formulations having a corresponding release profile may be prepared. An example of such a formulation is an osmotically driven release system for achieving a delayed release of one component via a coating that itself contains the other component which is accordingly released earlier. In a release system of this kind, which is particularly suitable for oral administration, at least part, and preferably all, of the surface of the release system, preferably those parts that will come into contact with the release medium, is/are semipermeable, preferably equipped with a semipermeable coating, so the surface(s) is/are permeable to the release medium, but substantially, preferably entirely, impermeable to the active ingredient, the surface(s) and/or optionally the coating comprising at least one opening for releasing the active ingredient. Moreover, precisely that/those surface(s) that is/are in contact with the release medium is/are provided with a coating containing and releasing the other component. This is preferably taken to mean a system in tablet form comprising a release opening, an osmotic pharmaceutical composition core, a semipermeable membrane and a polymer portion that exerts pressure upon swelling. A suitable example of this kind of system is the system distributed by ALZA Corporation, USA under the tradenames OROS®, in particular, the OROS® Push-Pull™ System, the OROS® Delayed Push-Pull™ System, the OROS® Multi-Layer PushPull™ system, the OROS® Push-Stick System and also, in specific cases, the LOROS™.

Embodiments and examples of osmotically driven release systems are, for example, disclosed in U.S. Pat. Nos. 4,765,989, 4,783,337 and 4,612,008, the entire disclosure of each of which is incorporated herein by reference.

A further example of a suitable pharmaceutical formulation is a gel-matrix tablet, such as the products developed by Penwest Pharmaceuticals (for example, under TimeRX). Suitable examples are provided in U.S. Pat. Nos. 5,330,761, 5,399,362, 5,472,711 and 5,455,046, the entire disclosure of each of which is incorporated herein by reference. Particularly suitable is a retarding matrix formulation, with an inhomogeneous distribution of the pharmaceutically active composition, whereby, for example, one component can be distributed in the outer region (the portion that comes into contact with the release medium most quickly) of the matrix and the other component is distributed inside the matrix. On contact with the release medium, the outer matrix layer initially (and rapidly) swells and firstly releases the first component, followed by the significantly (more) retarded release of the other component. Examples of a suitable matrix include matrices with 1 to 80% by weight of one or more hydrophilic or hydrophobic polymers as pharmaceutically acceptable matrix formers. A further example of a suitable matrix may be inferred from U.S. Pat. No. 4,389,393 the respective contents of which hereby being incorporated by reference and forming part of the disclosure of the present invention.

The amount of the inventive pharmaceutically active combination to be administered to the patient may vary depending on different factors well known to those skilled in the art, for example, the weight of the patient, the route of administration, or the severity of the illness.

In a further aspect the present invention relates to the use of an inventive combination as described herein for the treatment of pain, said pain preferably including but not being limited to inflammatory pain, neuropathic pain, acute pain, chronic pain, visceral pain, migraine pain and cancer pain.

In another aspect the present invention relates to the use of an inventive combination as described herein for the preparation of a medicament for the treatment of pain, said pain preferably including but not being limited to inflammatory pain, neuropathic pain, acute pain, chronic pain, visceral pain, migraine pain and cancer pain.

In another aspect the present invention relates to a method of treating pain in a mammal, preferably a human, which comprises administering an effective amount of an inventive combination as described herein to the mammal.

Pharmacological Test Methods:

In Vivo Experiments According to Chung

The weight ratios of components (a) and (b) that will lead to a supra-additive effect/synergistic effect of the inventive compositions may be determined in the test of Kim & Chung as described in Kim S H, Chung J M. An experimental model for peripheral mononeuropathy produced by segmental spinal nerve ligation in the rat. Pain 1992; 50: 355-63. Said reference is hereby incorporated by reference and forms part of the disclosure.

Ligatures were applied to the left L5/L6 spinal nerves of male Sprague-Dawley rats (140-160 g body weight, Janvier, Genest St. Isle, France). Animals developed tactile allodynia at the ipsilateral paw. Three to four weeks after the operation the tactile allodynia threshold baseline (withdrawal threshold) was measured on the ipsilateral and contralateral hind paw by an electronic von Frey anaesthesiometer (Somedic, Schweden). After test and measurement of the baseline, (1R,2R)-3-(3-dimethylamino-1-ethyl-2-methyl-propyl)-phenol hydrochloride (hereinafter referred to as tapentadol hydrochloride or tapentadol-HCl), (S)-pregabalin as well as the inventive combination of tapentadol-HCl and (S)-pregabalin were each dissolved in 0.9% NaCl solution and injected by the intravenous (i.v.) route (application volume 5 ml/kg). Animals were randomly assigned to groups of 10 for each test dose and vehicle (0.9% NaCl solution) and tactile withdrawal thresholds were tested 0.5 h before administration and on several time points (0.5, 1 and 3 hours) after intravenous administration. Ipsi- and contralateral hindpaws were tested. The median of the withdrawal threshold for each animal at a given time is calculated from five individual stimulations with the electronic von Frey filament. Withdrawal thresholds of the injured paws are expressed as % MPE (Maximum possible effect) comparing predrug threshold of Chung-Animals (=0% MPE) and control threshold of sham-animals (100% MPE). A cut-off is set at 100% MPE. The effect of each compound and vehicle is calculated for each testing time point as interindividual % MPE value.

Data (anti-allodynic efficacy (% MPE), ipsi-lateral, paw withdrawal threshold (g), ipsi- and conralateral) were analysed by means of a two-factor analysis of variance (ANOVA) with repeated measures. In case of a significant treatment effect, post hoc analysis with Bonferroni adjustment was performed. Results were considered statistically significant if P<0.05. $ED_{50}$ values and 95% confidence intervals (95% CI) were determined for the anti-allodynic efficacy (% MPE) at the time of the peak effect for each drug by regression analysis. The analysis of the results was carried out via statistical comparison of the theoretical additive $ED_{50}$-value with the experimentally determined $ED_{50}$-value of a so-called fixed ratio combination (isobolographic analysis according to Tallarida R J, Porreca F, and Cowan A. Statistical analysis of drug-drug and site-site interactions with isobolograms. Life Sci 1989; 45: 947-61, which is hereby incorporated by reference.

Results:

Tapentadol hydrochloride (0.1, 0.316, 1, 3.16 and 10 mg/kg i.v.) showed a dose dependent increase in the withdrawal threshold of the ipsi-lateral hind paw with an efficacy of 94% MPE and an $ED_{50}$-value (95% confidence interval) of 1.65 (1.20-2.35) mg/kg i.v. calculated from the peak effect vs. control values at 30 min. after administration.

(S)-Pregabalin (0.1, 3.16 and 10 mg/kg i.v.) showed a dose dependent increase in the withdrawal threshold of the ipsi-lateral hind paw with an efficacy of 67% MPE and an $ED_{50}$-value (95% confidence interval) of 4.20 (3.37-5.43) mg/kg i.v. calculated from the peak effect vs. control values at 30 min. after administration.

Tapentadol hydrochloride and (S)-pregabalin show a potency difference which amounts to a factor 2.5 based on the $ED_{50}$ values 30 minutes after administration. Combinations in a fixed ratio of 1:2.5 (tapentadol hydrochloride:(S)-pregabalin) were tested in doses of 0.1 mg/kg+0.25 mg/kg; 0.3 mg/kg+0.75 mg/kg, 1 mg/kg+2.5 mg/kg i.v. tapentadol hydrochloride+(S)-pregabalin, respectively. These combinations showed a dose dependent increase in the withdrawal threshold of the ipsi-lateral hind paw. The highest dose combination tested showed full efficacy with 89% MPE. Potency was quantified by an $ED_{50}$ value (95% confidence interval) of 0.83 (0.74-0.92) mg/kg i.v. calculated from the peak effect vs control values at 30 min after administration.

The results of the isobolographic analysis are summarized in the following Table 1.

TABLE 1

Experimental $ED_{50}$ values of tapentadol hydrochloride and (S)-pregabalin and isobolographic analysis of the interaction between tapentadol hydrochloride and (S)-pregabalin:

| | tapentadol-HCl | (S)-pregabalin | Theoretical $ED_{50}$ of the combination of tapentadol-HCl and (S)-pregabalin | Experimental $ED_{50}$ of the combination of tapentadol-HCl and (S)-pregabalin | interaction |
|---|---|---|---|---|---|
| Substance/ $ED_{50}$ [mg/kg i.v.] (95% confidence interval) | 1.65 (1.20-2.35) | 4.20 (3.37-5.43) | 2.91 (2.28-3.54) | 0.83 (0.74-0.92) | synergistic (p < 0.001) | p: Level of statistical significance

The experimental $ED_{50}$ value (95% confidence interval) of 0.83 (0.74-0.92) mg/kg i.v. of the inventive combination is below the theoretical additive $ED_{50}$ value (95% confidence interval) of 2.91 (2.28-3.54) mg/kg i.v. and is statistically significant (p<0.001) as compared to the line of additivity. Thus, the interaction of tapentadol hydrochloride and (S)-pregabalin is synergistic.

Analysis of contra-lateral paw withdrawal thresholds reveal significant anti-nociceptive effects of tapentadol hydrochloride and (S)-pregabalin at 10 mg/kg i.v. while no significant anti-nociceptive effect was seen at the highest dose of the inventive combination. Thus, synergistic anti-allodynic activity of tapentadol hydrochloride and (S)-pregabalin result in reduced anti-nociceptive side effects.

b) In Vivo Experiments According to Chung

Experimental Preparation

Under pentobarbital anaesthesia (Narcoren®, 60 mg/kg i.p., Merial GmbH, Hallbergmoos, Germany), the L5, L6 spinal nerves were tightly ligated (Kim and Chung, Pain 1992; 50: 355). The left L5 and L6 spinal nerves were exposed by removing a small piece of the paravertebral muscle and a part of the left spinous process of the L5 lumbar vertebra. The L5 and L6 spinal nerves were then carefully isolated and tightly ligated with silk (NC-silk black, USP 5/0, metric 1, Braun Melsungen AG, Melsungen, FRG). After checking hemostasis, the muscle and the adjacent fascia were closed with sutures and the skin was closed with sutures.

Anti-Allodynic Testing

After operation, animals were allowed to recover for one week. Animals develop tactile allodynia which is stable for at least five weeks. For the assessment of tactile allodynia the rats were placed on a metal mesh covered with a plastic dome and were allowed to habituate until the exploratory behaviour diminished. Threshold for tactile allodynia was measured with an electronic von Frey anesthesiometer (Somedic, Sweden). Animals randomly assigned to groups of 10 for each test dose and vehicle, were tested 0.5 h before administration and on several time points after administration. The median of the withdrawal threshold for each animal at a given time is calculated from five individual stimulations with the electronic von Frey filament. Withdrawal thresholds of the injured paws are expressed as % maximal possible effect (% MPE) comparing predrug threshold of Chung-animals (=0% MPE) and control threshold of sham-animals (=100% MPE). A cut-off is set at 100% MPE. The effect of each compound and vehicle is calculated for each testing time point (e.g. 0.5, 1, 3 h post administration) as interindividual % MPE value (±SEM). Anti-allodynic efficacy is defined as increase of ipsi-lateral withdrawal threshold without effect on contra-lateral withdrawal threshold. Ten animals have been used in each group.

Data Analysis

Effects of drug combinations are compared to the theoretical sum of the effects of each drug tested alone. Drug combination effects which are clearly greater than the sum of the single drug effects are considered to be supra-additive.

TABLE 2

| | | Effect | |
|---|---|---|---|
| Treatment | | % MPE (time after administration of | |
| Compound A Dose mg/kg | Compound B Dose mg/kg | Tapentadol hydrochloride) | Comment |
| Example 2.1 (combination of Tapentadol hydrochloride with Topiramate or Levetiracetam) | | | |
| Tapentadol hydrochloride 1 mg/kg iv | | 18 ± 4% (30 min) | |
| | Topiramate 1 mg/kg iv | 22 ± 3% (30 min) | |
| Tapentadol hydrochloride 1 mg/kg iv | Topiramate 1 mg/kg iv | 87 ± 3% (30 min) | Supra-additive vs 18 + 22 = 40 |
| | Levetiracetam 20 mg/kg iv | 16 ± 4% (30 min) | |
| Tapentadol hydrochloride 1 mg/kg iv | Levetiracetam 20 mg/kg iv | 48 ± 3% (30 min) | Supra-additive vs 18 + 16 = 34 |
| Example 2.2 (combination of Tapentadol hydrochloride with Gabapentin) | | | |
| Tapentadol hydrochloride 1 mg/kg iv | | 13 ± 5% (30 min) | |
| | Gabapentin 10 mg/kg iv (20 min before Tapentadol hydrochloride) | 3 ± 3% (30 min) | |
| Tapentadol hydrochloride 1 mg/kg iv | Gabapentin 10 mg/kg iv (20 min before Tapentadol hydrochloride) | 34 ± 5% (30 min) | Supra-additive vs 13 + 3 = 16 |
| Example 2.3 (combination of Tapentadol with Lacosamide) | | | |
| Tapentadol hydrochloride 1 mg/kg iv | | 13 ± 5% (30 min) | |
| | Lacosamide 3 mg/kg iv | 24 ± 4% (30 min) | |
| Tapentadol hydrochloride 1 mg/kg iv | Lacosamide 3 mg/kg iv | 39 ± 9% (30 min) | Additive vs 13 + 24 = 37 | c) In Vivo Experiments According to Randall-Selitto

The weight ratios of the components (a) and (b) that will lead to a supra-additive effect (synergistic effect) of the inventive pharmaceutical composition may be determined via the test of Randall and Selitto as described in Arch. Int. Pharmacodyn., 1957, 111, 409 to 419, which is a model for inflammatory pain. The respective part of the literature is hereby incorporated by reference and forms part of the present disclosure.

Acute inflammation is induced by an intraplantar injection of 0.1 ml of a carrageenan solution (0.5% in distilled water) into one hind paw. The mechanical nociceptive threshold is measured 4 hours after carrageenan injection using an Algesiometer (Ugo Basile, Italy). The device generates a mechanical force with a linear increase over time. The force is applied to the dorsal surface of the inflamed rat hind paw via a cone-shaped stylus with a rounded tip (2 mm tip diameter). The nociceptive threshold is defined as the force (in grams) at which the rat vocalises (cut-off force 250 g). The mechanical nociceptive threshold is measured at different timepoints after the drug or vehicle administration. The antinociceptive and antihyperalgesic activity of the tested substance is expressed as percentages of the maximal possible effect (% MPE). The group size is n=10.

The analysis of the results with respect to a supra-additive effect of the inventive pharmaceutical composition comprising the components (a) and (b) is carried out via statistical comparison of the theoretical additive $ED_{50}$-value with the experimentally determined $ED_{50}$-value of a so-called fixed ratio combination (isobolographic analysis according to Tallarida J T, Porreca F, and Cowan A. Statistical analysis of drug-drug and site-site interactions with isobolograms. Life Sci 1989; 45: 947-961, which is hereby incorporated by reference).

The interactions studies presented herein were performed using equieffective doses of the two components, calculated from the ratio of the respective $ED_{50}$ values of the components if administered alone.

The route of administration was intravenous (i.v.) for Tapentadol hydrochloride (A) and intraperitoneal (i.p.) for the anticonvulsants (antiepileptics) Lamotrigine, Lacosamide, Levetiracetam and Retigabine dihydrochloride. When A was applied alone, the peak effect was reached 15 min p. appl. (timepoint of first measurement) and an $ED_{50}$-value of 1.75 (1.69-1.81) mg/kg i.v. was calculated. The anticonvulsants induced dose-dependent analgesic effects with $ED_{50}$-values of 35.3 (32.7-38.1) mg/kg i.p. (Lamotrigine), 35.85 (34.74-36.89) mg/kg i.p. (Lacosamide), 986.0 (854.0-1137.3) (Levetiracetam) mg/kg i.p. and 5.09 (4.68-5.50) mg/kg i.p. (Retigabine dihydrochloride), reaching the peak effect 15 min p. appl. According to their respective timepoint of peak effect, A was applied 15 min and the anticonvulsant component 15 min before timepoint of measurement of the interaction-experiments (i. e. both components were applied simultaneously). Thus, the time point of $ED_{50}$ calculation of the combination corresponds to the timepoint of the peak effect of the respective compound. The isobolographic analysis revealed that the experimental $ED_{50}$-values of the combinations were significantly lower than the respective theoretical $ED_{50}$-values. Thus, the combination studies demonstrate superadditive/supraadditive interaction of A with all of the anticonvulsants, Lamotrigine, Lacosamide, Levetiracetam and Retigabine dihydrochloride.

The results of the isobolographic analysis are summarized in the following Table 3:

Experimental $ED_{50}$ values of A, Lamotrigine, Lacosamide, Levetiracetam and Retigabine dihydrochloride and isobolographic analysis of the interaction between A with these anticonvulsants, respectively.

TABLE 3

Experimental $ED_{50}$ values of Tapentadol (A), Lamotrigine, Lacosamide, Levetiracetam and Retigabine dihydrochloride, and isobolographic analysis of the interaction between A with, Lamotrigine, Lacosamide, Levetiracetam or Retigabine dihydrochloride, respectively.

| | $ED_{50}$ [mg/kg] | | | | | | | |
|---|---|---|---|---|---|---|---|---|
| Substance | A | Lamotrigine | Lacosamide | Levetiracetam | Retigabine dihydrochloride | Theoretical $ED_{50}$ of the combination | Experimental $ED_{50}$ of combination | Interaction |
| A + Lamotrigine | 1.747 (1.689-1.805) * | 35.25 (32.74-38.08) | — | — | — | 18.50 (17.74-19.26) | 17.51 (16.69-18.40) | additive to supra-additive ($p < 0.05$) |
| A + Lacosamide | 1.747 (1.689-1.805) * | — | 35.85 (34.74-36.89) | — | — | 18.80 (18.38-19.21) | 15.24 (14.42-15.95) | supra-additive ($p < 0.001$) |
| A + Levetiracetam | 1.747 (1.689-1.805) * | — | — | 986.0 (854.0-1137.3) | — | 493.8 (458.0-529.7) | 416 (393.5-442.4) | supra-additive ($p < 0.001$) |
| A + Retigabine dihydrochloride | 1.749 (1.646-1.849) | — | — | — | 5.09 (4.68-5.50) | 3.42 (3.25-3.59) | 1.82 (1.71-1.94) | supra-additive ($p < 0.001$) |

* identical single-substance group with A for these combinations
p: level of statistical significance of supra-additive interaction The weight ratios of A to the respective anticonvulsant component used in the afore mentioned experiments were as follows:

| Combination of A with | Ratio |
|---|---|
| Lamotrigine | 1:20.2 |
| Lacosamide | 1:20.5 |
| Levetiracetam | 1:564 |
| Retigabine dihydrochloride | 1:2.9 |

The foregoing description and examples have been set forth merely to illustrate the invention and are not intended to be limiting. Since modifications of the described embodi-

The invention claimed is:

1. A composition of matter comprising in combination:
   (a) a 3-(3-dimethylamino-1-ethyl-2-methyl-propyl)-phenol compound corresponding to formula (I):

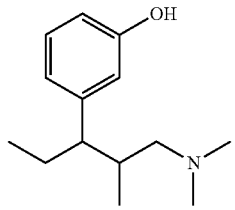

or a pharmaceutically acceptable salt thereof, and
   (b) at least one antiepileptic selected from the group consisting of topiramate, lamotrigine, lacosamide, levetiracetam and retigabine.

2. A composition of matter as claimed in claim 1, wherein said 3-(3-dimethylamino-1-ethyl-2-methyl-propyl)-phenol compound is present in the form of an isolated stereoisomer.

3. A composition of matter as claimed in claim 1, wherein said 3-(3-dimethylamino-1-ethyl-2-methyl-propyl)-phenol compound is present in the form of a mixture of stereoisomers in any mixing ratio.

4. A composition of matter as claimed in claim 3, wherein said mixture is a racemic mixture.

5. A composition of matter as claimed in claim 1, wherein the compound of formula (I) is selected from the group consisting of:
   (1R,2R)-3-(3-dimethylamino-1-ethyl-2-methyl-propyl)-phenol,
   (1S,2S)-3-(3-dimethylamino-1-ethyl-2-methyl-propyl)-phenol,
   (1R,2S)-3-(3-dimethylamino-1-ethyl-2-methyl-propyl)-phenol,
   (1S,2R)-3-(3-dimethylamino-1-ethyl-2-methyl-propyl)-phenol an acid addition salt of any of the foregoing, and
   mixtures of two or more of the foregoing.

6. A composition of matter as claimed in claim 5, wherein said compound of formula (I) is selected from the group consisting of:
   (1R,2R)-3-(3-dimethylamino-1-ethyl-2-methyl-propyl)-phenol,
   (1S,2S)-3-(3-dimethylamino-1-ethyl-2-methyl-propyl)-phenol, an acid addition salt of any of the foregoing, and
   mixtures thereof.

7. A composition of matter as claimed in claim 6, wherein said compound of formula (I) is (1R,2R)-3-(3-dimethylamino-1-ethyl-2-methyl-propyl)-phenol of formula (I'),

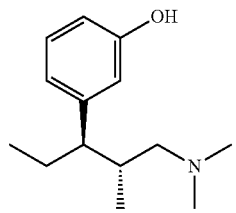

or an acid addition salt thereof.

8. A composition of matter as claimed in claim 7, wherein said compound of formula (I) is a hydrochloride salt of (1R,2R)-3-(3-dimethylamino-1-ethyl-2-methyl-propyl)-phenol.

9. A composition of matter as claimed in claim 1, wherein the antiepileptic is topiramate.

10. A composition of matter as claimed in claim 1, wherein the antiepileptic is lamotrigine.

11. A composition of matter as claimed in claim 1, wherein the antiepileptic is lacosamide.

12. A composition of matter as claimed in claim 1, wherein the antiepileptic is levetiracetam.

13. A composition of matter as claimed in claim 1, wherein the antiepileptic is retigabine.

14. A composition of matter as claimed in claim 1, wherein the two components (a) and (b) are present in the form of a salt formed from said two components.

15. A composition of matter as claimed in claim 1, wherein said 3-(3-dimethylamino-1-ethyl-2-methyl-propyl)-phenol compound or salt thereof and said antiepileptic are present in a weight ratio such that the composition exerts a synergistic effect upon administration to a patient.

16. A composition of matter as claimed in claim 1, further comprising at least one pharmaceutical carrier or auxiliary agent.

17. A composition of matter as claimed in claim 16, wherein said composition is formed into a dosage form suitable for oral, intravenous, intraarterial, intraperitoneal, intradermal, transdermal, intrathekal, intramuscular, intranasal, transmucosal, subcutaneous, or rectal administration.

18. A composition of matter as claimed in claim 17, wherein said antiepileptic is present in controlled-release form.

19. A composition of matter as claimed in claim 16, wherein said composition comprises caffeine.

20. A method of treating or inhibiting pain in a subject in need thereof, said method comprising administering to said subject a pharmacologically effective amount of a composition as claimed in claim 1.

21. A method as claimed in claim 20, wherein said pain is selected from the group consisting of inflammatory pain, neuropathic pain, acute pain, chronic pain, visceral pain, migraine pain and cancer pain.

22. A method as claimed in claim 20, wherein said 3-(3-dimethylamino-1-ethyl-2-methyl-propyl)-phenol compound and said antiepileptic are administered simultaneously either by the same or by different pathways of administration.

23. A method as claimed in claim 20, wherein said 3-(3-dimethylamino-1-ethyl-2-methyl-propyl)-phenol compound and said antiepileptic are administered sequentially either by the same or by different pathways of administration, with the 3-(3-dimethylamino-1-ethyl-2-methyl-propyl)-phenol compound being administered before the antiepileptic.

24. A method as claimed in claim 20, wherein said 3-(3-dimethylamino-1-ethyl-2-methyl-propyl)-phenol compound and said antiepileptic are administered sequentially either by the same or by different pathways of administration, with the 3-(3-dimethylamino-1-ethyl-2-methyl-propyl)-phenol compound being administered after the antiepileptic.

25. A composition of matter as claimed in claim 17, wherein component (b) is present in controlled-release form.

* * * * *